US009808000B2

(12) United States Patent
Takabe et al.

(10) Patent No.: US 9,808,000 B2
(45) Date of Patent: Nov. 7, 2017

(54) WATER DISPERSIBLE GRANULES

(71) Applicant: Sumitomo Chemical Company, Limited, Tokyo (JP)

(72) Inventors: Rie Takabe, Takarazuka (JP); Seiji Iuchi, Tokyo (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 14/770,669

(22) PCT Filed: Feb. 24, 2014

(86) PCT No.: PCT/JP2014/055198
§ 371 (c)(1),
(2) Date: Aug. 26, 2015

(87) PCT Pub. No.: WO2014/133178
PCT Pub. Date: Sep. 4, 2014

(65) Prior Publication Data
US 2016/0007592 A1    Jan. 14, 2016

(30) Foreign Application Priority Data
Feb. 28, 2013  (JP) ................................. 2013-038545

(51) Int. Cl.
| | | |
|---|---|---|
| A01N 25/14 | (2006.01) | |
| A01N 43/56 | (2006.01) | |
| A01N 43/80 | (2006.01) | |
| A01N 47/14 | (2006.01) | |
| A01N 47/44 | (2006.01) | |
| C05G 3/02 | (2006.01) | |
| C05G 3/00 | (2006.01) | |

(52) U.S. Cl.
CPC ............. *A01N 25/14* (2013.01); *A01N 43/56* (2013.01); *A01N 43/80* (2013.01); *A01N 47/14* (2013.01); *A01N 47/44* (2013.01); *C05G 3/0005* (2013.01); *C05G 3/0058* (2013.01); *C05G 3/0064* (2013.01); *C05G 3/02* (2013.01)

(58) Field of Classification Search
CPC .... A01N 2300/00; A01N 43/40; A01N 37/50; A01N 53/00; A01N 25/04; A01N 37/26; A01N 37/40; A01N 43/56; A01N 43/653; A01N 43/707; A01N 43/80; A01N 43/82; A01N 47/02; A01N 47/22; A01N 47/24
See application file for complete search history.

(56) References Cited

U.S. PATENT DOCUMENTS

| | | | |
|---|---|---|---|
| 5,723,141 A | 3/1998 | Kimura et al. | |
| 2001/0014347 A1* | 8/2001 | Koike ................ | A01N 25/14 424/409 |
| 2006/0013846 A1* | 1/2006 | Kurita ................ | A01N 25/30 424/405 |
| 2006/0166898 A1* | 7/2006 | Chen ................... | A01N 25/04 514/22 |

FOREIGN PATENT DOCUMENTS

| | | | | |
|---|---|---|---|---|
| CN | 101785456 A | 7/2010 | | |
| JP | H05194105 A | 8/1993 | | |
| JP | H07101812 A | 4/1995 | | |
| JP | 2000204003 A | 7/2000 | | |
| JP | 2002284602 A | 10/2002 | | |
| JP | 2004026683 A | 1/2004 | | |
| JP | 2004026685 A | 1/2004 | | |
| JP | WO200403699 A1 * | 5/2004 | ............. | A01N 25/14 |
| JP | WO2004/036994 A1 * | 5/2005 | ............. | A01N 25/14 |
| JP | 2005170932 A | 6/2005 | | |
| JP | 2005187452 A | 7/2005 | | |
| WO | 2004036994 A1 | 5/2004 | | |

OTHER PUBLICATIONS

Office Action dated Jul. 26, 2017 in JP Application No. 2015-503075.
Yonemura, "Water Dispersible Granules", Noyaku Seizai Gaido, Japan Plant Protection Association, 3 pgs (2013).

* cited by examiner

*Primary Examiner* — Audrea Buckley
(74) *Attorney, Agent, or Firm* — Panitch Schwarze Belisario & Nadel LLP

(57) ABSTRACT

Water dispersible granules are provided containing (a) an agrochemical active ingredient that is solid at 25° C., (b) a polyoxyalkylene alkyl ether phosphate or its salt, (c) at least one anionic surfactant selected from the group consisting of arylsulfonates or their formaldehyde condensates, ligninsulfonates, and polycarboxylates, and (d) lactose. The granules are water dispersible granules having good disintegrability and dispersibility in water and also having good storage stability. The water dispersible granules can be disintegrated and dispersed in a small amount of water. Accordingly, the water dispersible granules can be mixed with paste fertilizers to produce agrochemical-containing paste fertilizers, which can also be used in paddy fields and are useful water dispersible granules.

21 Claims, No Drawings

WATER DISPERSIBLE GRANULES

CROSS-REFERENCE TO RELATED APPLICATION

This application is a Section 371 of International Application No. PCT/JP2014/055198, filed Feb. 24, 2014, which was published in the Japanese language on Sep. 4, 2014, under International Publication No. WO 2014/133178 A1, and the disclosure of which is incorporated herein by reference.

TECHNICAL FIELD

The present invention relates to water dispersible granules comprising agrochemical active ingredients and having good disintegrability and dispersibility.

BACKGROUND ART

Water dispersible granules comprising agrochemical active ingredients are described in, for example, JP-A-06-92803 and JP-A-2002-284602.

An object of the present invention is to provide water dispersible granules comprising an agrochemical active ingredient and having good disintegrability and dispersibility.

DISCLOSURE OF THE INVENTION

The intensive study of the present inventors to find water dispersible granules that are readily disintegrated and dispersed when introduced into water has found that the following water dispersible granules have good disintegrability and dispersibility in water, completing the present invention.

The present invention is as follows.

[1] Water dispersible granules, comprising: (a) an agrochemical active ingredient that is solid at 25° C.; (b) a polyoxyalkylene alkyl ether phosphate or its salt; (c) at least one anionic surfactant selected from the group consisting of arylsulfonates or their formaldehyde condensates, ligninsulfonates, and polycarboxylates; and (d) lactose.

[2] The water dispersible granules according to [1], comprising: 1 to 80 wt % of (a) the agrochemical active ingredient that is solid at 25° C., 0.1 to 10 wt % of (b) the polyoxyalkylene alkyl ether phosphate or its salt; 0.1 to 20 wt % of the total of (c) the at least one anionic surfactant selected from the group consisting of arylsulfonates or their formaldehyde condensates, ligninsulfonates, and polycarboxylates; and 10 to 98.8 wt % of (d) lactose.

[3] The water dispersible granules according to [2], comprising: 0.1 to 10 wt % of the total of (c) the at least one anionic surfactant selected from the group consisting of arylsulfonates or their formaldehyde condensates, ligninsulfonates, and polycarboxylates.

[4] The water dispersible granules according to any one of [1] to [3], wherein the weight ratio of (b) the polyoxyalkylene alkyl ether phosphate or its salt to the total of (c) the at least one anionic surfactant selected from the group consisting of arylsulfonates or their formaldehyde condensates, ligninsulfonates, and polycarboxylates is from 1:0.5 to 1:15.

[5] The water dispersible granules according to any one of [1] to [3], wherein the weight ratio of (b) the polyoxyalkylene alkyl ether phosphate or its salt to the total of (c) the at least one anionic surfactant selected from the group consisting of arylsulfonates or their formaldehyde condensates, ligninsulfonates, and polycarboxylates is from 1:0.5 to 1:10.

[6] The water dispersible granules according to any one of [1] to [3], wherein the weight ratio of (b) the polyoxyalkylene alkyl ether phosphate or its salt to the total of (c) the at least one anionic surfactant selected from the group consisting of arylsulfonates or their formaldehyde condensates, ligninsulfonates, and polycarboxylates is from 1:1.5 to 1:7.5.

[7] The water dispersible granules according to any one of [1] to [6], wherein (b) the polyoxyalkylene alkyl ether phosphate or its salt is a sodium salt of polyoxyalkylene alkyl ether phosphate.

[8] The water dispersible granules according to any one of [1] to [7], wherein (c) the at least one anionic surfactant selected from the group consisting of arylsulfonates or their formaldehyde condensates, ligninsulfonates, and polycarboxylates is an arylsulfonate or its formaldehyde condensate.

[9] The water dispersible granules according to [8], wherein the arylsulfonate or its formaldehyde condensate is a formaldehyde condensate of naphthalenesulfonate.

[10] The water dispersible granules according to [9], wherein the arylsulfonate or its formaldehyde condensate is a formaldehyde condensate of sodium naphthalenesulfonate.

[11] The water dispersible granules according to any one of [1] to [10], wherein (a) the agrochemical active ingredient that is solid at 25° C. is an insecticidal ingredient and/or fungicidal ingredient.

[12] The water dispersible granules according to [11], wherein (a) the agrochemical active ingredient that is solid at 25° C. is at least one selected from the group consisting of neonicotinoid insecticides, nereistoxin insecticides, fungicides having an activity against *Magnaporthe grisea*, and fungicides having an activity against *Rhizoctonia solani*.

[13] The water dispersible granules according to [11], wherein (a) the agrochemical active ingredient that is solid at 25° C. is at least one selected from the group consisting of neonicotinoid insecticides and fungicides having an activity against *Magnaporthe grisea*.

[14] The water dispersible granules according to [12], wherein (a) the agrochemical active ingredient that is solid at 25° C. is at least one selected from the group consisting of clothianidin, cartap, isotianil, and furametpyr.

[15] The water dispersible granules according to [13], wherein (a) the agrochemical active ingredient that is solid at 25° C. is at least one selected from the group consisting of clothianidin and isotianil.

[16] A method for producing water dispersible granules, comprising: adding water to a mixture containing (a) an agrochemical active ingredient that is solid at 25° C., (b) a polyoxyalkylene alkyl ether phosphate or its salt, (c) at least one anionic surfactant selected from the group consisting of arylsulfonates or their formaldehyde condensates, ligninsulfonates, and polycarboxylates, and (d) lactose; kneading the mixture; and granulating the kneaded mixture by a wet extrusion granulation method.

[17] A use of the water dispersible granules according to any one of [1] to [15] for mixing with a paste fertilizer or liquid fertilizer.

[18] A method for producing an agrochemical-containing paste fertilizer or agrochemical-containing liquid fertilizer, comprising a step of mixing the water dispersible granules according to any one of [1] to [15] with a paste fertilizer or liquid fertilizer.

[19] An agrochemical-containing paste fertilizer, comprising (a) an agrochemical active ingredient that is solid at 25° C., (b) a polyoxyalkylene alkyl ether phosphate or its salt, (c) at least one anionic surfactant selected the group consisting of arylsulfonates or their formaldehyde condensates, ligninsulfonates, and polycarboxylates, (d) lactose, and (e) a fertilizer ingredient.

[20] An agrochemical-containing liquid fertilizer, comprising (a) an agrochemical active ingredient that is solid at 25° C., (b) a polyoxyalkylene alkyl ether phosphate or its salt, (c) at least one anionic surfactant selected the group consisting of arylsulfonates or their formaldehyde condensates, ligninsulfonates, and polycarboxylates, (d) lactose, and (e) a fertilizer ingredient.

[21] A method for applying an agrochemical, comprising side-dressing the agrochemical-containing paste fertilizer according to [19].

[22] A method for applying an agrochemical, comprising side-dressing the agrochemical-containing liquid fertilizer according to [20].

The water dispersible granules of the present invention are water dispersible granules having good disintegrability and dispersibility that are readily disintegrated and dispersed in water.

The water dispersible granules of the present invention are water dispersible granules having good manufacturability and also having good storage stability.

The water dispersible granules of the present invention can be readily disintegrated and dispersed not only in a typical amount of water used for water dispersible granules, but also in a much less amount of water than typical (for example, the same weight as the water dispersible granules of the present invention).

Paste fertilizers have been recently used in the agricultural field. Paste fertilizers refer to past fertilizers having viscosity and intermediate properties between solid fertilizers and liquid fertilizers. Since having both fertilizing effect and agrochemical activity may reduce agricultural work, paste fertilizers containing agrochemical active ingredients have been also used by utilizing water dispersible granules containing agrochemical active ingredients. However, a large amount of water in paste fertilizers to be used in paddy fields reduces the viscosity of the paste fertilizers. Thus, water dispersible granules for paste fertilizers are desirably disintegrated and dispersed in a small amount of water and also desirably dispersed well in paste fertilizers.

The water dispersible granules of the present invention are disintegrated and dispersed in a small amount of water as described above, and furthermore a concentrated aqueous dispersion of the water dispersible granules of the present invention is dispersed well in a paste fertilizer. Therefore, the water dispersible granules of the present invention are also useful for paste fertilizers. In addition, paste fertilizers obtained using the water dispersible granules of the present invention are good paste fertilizers with less uneven distribution of the agrochemical active ingredients.

MODE FOR CARRYING OUT THE INVENTION

The water dispersible granules of the present invention comprise an agrochemical active ingredient that is solid at 25° C. (hereinafter may be referred to as a component (a)).

Examples of the component (a) used in the present invention may include insecticidal ingredients, fungicidal ingredients, herbicidal ingredients, insect growth regulators, plant growth regulators, and insect repellents.

Examples of insecticidal ingredients and insect growth regulators may include pyrethroid compounds, such as deltamethrin, tralomethrin, acrinathrin, and tetramethrin; carbamate compounds, such as propoxur, isoprocarb, xylylcarb, metolcarb, XMC, carbaryl, pirimicarb, carbofuran, methomyl, and phenoxycarb; organophosphorus compounds, such as acephate, trichlorfon, tetrachlorvinphos, dimethylvinphos, pyridaphenthion, azinphos-ethyl, and azinphos-methyl; urea compounds, such as diflubenzuron, chlorfluazuron, lufenuron, hexaflumuron, flufenoxuron, furcycloxuron, cyromazine, diafenthiuron, hexythiazox, novaluron, teflubenzuron, triflumuron, 4-chloro-2-(2-chloro-2-methylpropyl)-5-(6-iodo-3-pyridylmethoxy)pyridazin-3(2H)-one, 1-(2,6-difluorobenzoyl)-3-[2-fluoro-4-(trifluoromethyl)phenyl]urea, 1-(2,6-difluorobenzoyl)-3-[2-fluoro-4-(1,1,2,3,3,3-hexafluoropropoxy)phenyl]urea, 2-tert-butylimino-3-isopropyl-5-phenyl-3,4,5,6-tetrahydro-2-H-1,3,5-thiadiazon-4-one, 1-(2,6-difluorobenzoyl)-3-[2-fluoro-4-(1,1,2,2-tetrafluoroethoxy)phenyl]urea; neonicotinoid compounds, such as imidacloprid, acetamiprid, clothianidin, nitenpyram, thiamethoxam, thiacloprid, and dinotefuran; spinosyns, such as spinosad; diamide compounds, such as flubendiamide, chlorantraniliprole, and cyantraniliprole; nereistoxin compounds, such as cartap, bensultap, and thiocyclam; buprofezin, phenoxycarb, fenazaquin, fenpyroximate, pyridaben, hydramethylnon, thiodicarb, chlorfenapyr, fenpyroximate, pymetrozine, pyrimidifen, tebufenozide, tebufenpyrad, triazamate, indoxacarb, sulfluramid, melbemectin, avermectin, boric acid, and paradichlorobenzene.

Examples of fungicidal ingredients may include benzimidazole compounds, such as benomyl, carbendazim, thiabendazole, and thiophanate-methyl; phenylcarbamate compounds, such as diethofencarb; dicarboxyimide compounds, such as procymidone, iprodione, and vinclozolin; azole compounds, such as diniconazole, propenazole, epoxiconazole, tebuconazole, difenoconazole, cyproconazole, flusilazole, and triadimefon; acylalanine compounds, such as metalaxyl; carboxyamide compounds, such as furametpyr, mepronil, flutolanil, thifluzamide, and isotianil; organophosphorus compounds, such as tolclofos-methyl, fosetyl-aluminium, and pyrazophos; anilinopyrimidine compounds, such as pyrimethanil, mepanipyrim, and cyprodinil; cyanopyrrole compounds, such as fludioxonil and fenpiclonil; antibiotics, such as blasticidin S, kasugamycin, polyoxin, and validamycin; methoxyacrylate compounds, such as azoxystrobin, kresoxim-methyl, and metominostrobin; chlorothalonil, mancozeb, captan, folpet, tricyclazole, pyroquilon, probenazole, fthalide, cymoxanil, dimethomorph, acibenzolar-S-methyl, famoxadone, oxolinic acid, fluazinam, ferimzone, diclocymet, chlobenthiazone, isovaledione, tetrachloroisophthalonitrile, thiophthalimidoxybisphenoxyarsine, 3-iodo-2-propylbutylcarbamate, para-hydroxybenzoate, sodium dehydroacetate, potassium sorbate, and orysastrobin.

Suitable fungicidal ingredients used are compounds having an activity against *Rhizoctonia solani* and *Magnaporthe grisea*. Examples include furametpyr, kasugamycin, diclocymet, orysastrobin, ferimzone, probenazole, fthalide, blasticidin S, and isotianil.

Examples of herbicidal ingredients may include triazine compounds, such as atrazine and metribuzin; urea compounds, such as fluometuron and isoproturon; hydroxybenzonitrile compounds, such as bromoxynil and ioxynil; 2,6-dinitroaniline compounds, such as pendimethalin and trifluralin; allyloxyalkanoic acid compounds, such as 2,4-D, dicamba, fluroxypyr, and mecoprop; sulfonylurea compounds, such as bensulfuron-methyl, meturfuron-methyl, nicosulfuron, primisulfuron-methyl, and cyclosulfamuron; imidazolinone compounds, such as imazapyr, imazaquin, and imazethapyr; bispyribac Na salt, bisthiobac Na salt, acifluorfen Na salt, sulfentrazone, paraquat, flumetsulam, triflusulfuron-methyl, fenoxaprop-p-ethyl, diflufenican, norflurazon, isoxaflutole, glufosinate ammonium, glyphosate, bentazon, mefenacet, propanil, fluthiamide, flumiclorac pentyl, and flumioxazin.

Examples of plant growth regulators may include maleic hydrazide, chlormekat, ethephon, gibberellin, mepiquat chloride, thidiazuron, inabenfide, paclobutrazol, and uniconazole.

Examples of insect repellents may include 1S,3R,4R,6R-carane-3,4-diol and dipropyl 2,5-pyridinedicarboxylate.

The water dispersible granules of the present invention may comprise only one agrochemical active ingredient or may comprise two or more agrochemical active ingredients. The content of the agrochemical active ingredient is usually from 1 to 80 wt %, preferably from 5 to 80 wt %, more preferably from 10 to 60 wt % with respect to the water dispersible granules.

The water dispersible granules of the present invention comprise a polyoxyalkylene alkyl ether phosphate or its salt (hereinafter may be referred to as a component (b)).

Preferred examples of polyoxyalkylene alkyl ether phosphates include polyoxyethylene alkyl ether phosphate, polyoxypropylene alkyl ether phosphate, polyoxybutylene alkyl ether phosphate, and polyoxyethylene polyoxypropylene alkyl ether phosphate. Of these, polyoxyethylene alkyl ether phosphate is preferred.

The polyoxyalkylene alkyl ether phosphate or its salt is preferably a salt of polyoxyalkylene alkyl ether phosphate in terms of the storage stability of the water dispersible granules.

Examples of salts of polyoxyalkylene alkyl ether phosphates include sodium salts, potassium salts, ammonium salts, alkanolamine salts, calcium salts, magnesium salts of polyoxyalkylene alkyl ether phosphates, with sodium salts of polyoxyalkylene alkyl ether phosphates being preferred.

The water dispersible granules of the present invention may comprise only one polyoxyalkylene alkyl ether phosphate or its salt, or may comprise two or more polyoxyalkylene alkyl ether phosphates or their salts. The content of the polyoxyalkylene alkyl ether phosphate or its salt is usually from 0.1 to 10 wt %, preferably from 0.1 to 5 wt % with respect to the water dispersible granules of the present invention.

The water dispersible granules of the present invention comprise at least one anionic surfactant (hereinafter may be referred to as a component (c)) selected from the group consisting of arylsulfonates or their formaldehyde condensates, ligninsulfonates, and polycarboxylates.

Arylsulfonates refer to salts of arylsulfonic acids in which a sulfo group (—$SO_3H$) is directly bonded to an aromatic ring that may be substituted by a chain hydrocarbon group. Examples of chain hydrocarbon groups include $C_1$ to $C_4$ alkyl groups, such as a methyl group, isopropyl group, butyl group, and isobutyl group; examples of aromatic rings include benzene and naphthalene; and examples of salts include alkali metal salts such as a sodium salt. Examples of arylsulfonates include alkylnaphthalenesulfonate, and commercially available products thereof include Newkalgen BX-C (available from TAKEMOTO OIL & FAT CO., LTD.).

Formaldehyde condensates of arylsulfonates refer to formaldehyde condensates of the above arylsulfonates, and examples thereof include formaldehyde condensates of naphthalenesulfonates and formaldehyde condensates of alkylnaphthalenesulfonates. Commercially available products of formaldehyde condensates of naphthalenesulfonates include Newkalgen WG-2 (available from TAKEMOTO OIL & FAT CO., LTD.), and commercially available formaldehyde condensates of alkylnaphthalenesulfonates include DEMOL SN-B (available from Kao Corporation).

Examples of commercially available products of ligninsulfonates include Newkalgen WG-4 (available from TAKEMOTO OIL & FAT CO., LTD.), Reax 85A (available from MeadWestvaco Corporation), Reax 83A (available from MeadWestvaco Corporation), Reax 81A (available from MeadWestvaco Corporation), Ployfon H (available from MeadWestvaco Corporation), Ployfon O (available from MeadWestvaco Corporation), Ployfon T (available from MeadWestvaco Corporation), Ployfon F (available from MeadWestvaco Corporation), SANX P201 (available from Nippon Paper Industries Co., Ltd.), SANX P200 (available from Nippon Paper Industries Co., Ltd.), and SANX P252 (available from Nippon Paper Industries Co., Ltd.).

Polycarboxylates refer to polymer compounds in which some or all of the hydrogen ions of the carboxyl group in the molecule of polycarboxylic acid are substituted by cations, wherein the cations may be derived from basic substances. The polycarboxylic acid is a polymer compound containing 90 mol % or more of the structural unit derived from a carboxyl group-containing ethylenic unsaturated monomer with respect to 100 mol % of the total structural units. Examples of commercially available products of polycarboxylates include Newkalgen WG-5 (available from TAKEMOTO OIL & FAT CO., LTD.), GEROPON T/36 (available from Rhodia Nicca, Ltd.), and Sokalan CP5 Granules (available from BASF).

Preferred components (c) are arylsulfonates or their formaldehyde condensates in terms of the disintegrability and dispersibility of formulations and the suspensibility of agrochemical active ingredients. Of these, formaldehyde condensates of naphthalenesulfonates are more preferred and of these, a formaldehyde condensate of sodium naphthalenesulfonate is still more preferred.

The content of the component (c) is usually from 0.1 to 20 wt %, preferably from 0.5 to 15 wt %, more preferably 1 to 10 wt % with respect to the water dispersible granules of the present invention.

The weight ratio of the component (b) to the component (c) is preferably from 1:0.5 to 1:15 (component (b):component (c)), more preferably from 1:0.5 to 1:10, still more preferably from 1:1.5 to 1:7.5 in terms of the disintegrability and dispersibility as well as the granule hardness.

The total content of the component (b) and the component (c) is usually from 0.2 to 30 wt %, preferably from 0.5 to 15 wt %, more preferably from 1 to 10 wt % with respect to the water dispersible granules of the present invention in terms of the disintegrability and dispersibility as well as the granule hardness.

The water dispersible granules of the present invention comprise lactose (hereinafter may be referred to as a component (d)).

The lactose used in the present invention is not limited to any particular lactose. The mean particle size thereof is preferably from 16 to 290 μm, more preferably from 20 to 200 μm. The content of the lactose is usually from 10 to 98.8 wt %, preferably from 20 to 95 wt %, more preferably from 30 to 70 wt % with respect to the water dispersible granules.

The water dispersible granules of the present invention may further optionally comprise formulation adjuvants, such as a disintegrator, carrier, binder, pH adjuster, defoamer, nonionic surfactant, cationic surfactant, and amphoteric surfactant. The content of formulation adjuvants is usually from 0 to 30 wt % with respect to the water dispersible granules of the present invention.

Examples of disintegrators include agar, hydroxypropyl starch, carboxymethyl starch ether, tragacanth, gelatin, casein, carboxymethyl cellulose, and carboxymethyl cellulose calcium.

When the water dispersible granules of the present invention comprise a disintegrator, the content of the disintegrator is usually from 0.1 to 10 wt %, preferably from 0.1 to 5 wt % with respect to the water dispersible granules of the present invention.

Examples of carriers may include mineral carriers, plant carriers, synthetic carriers, and water-soluble carriers.

Examples of mineral carriers include kaolin minerals, such as kaolinite, dickite, nacrite, and halloysite; serpentines, such as chrysotile, lizardite, antigorite, and amesite; montmorillonite minerals, such as sodium montmorillonite, calcium montmorillonite, and magnesium montmorillonite; smectites, such as saponite, hectorite, sauconite, and hyderite; micas, such as pyrophyllite, talc, agalmatolite, muscovite, phengite, sericite, and illite; silicas, such as cristobalite and quartz; hydrated magnesium silicates, such as attapulgite and sepiolite; calcium carbonates, such as dolomite and calcium carbonate fine powder; sulfate minerals, such as gypsum and gypsum; zeolite, zeolite, tuff, vermiculite, laponite, pumice, diatomaceous earth, acid clay, and activated clay.

Examples of plant carriers include cellulose, chaff, wheat flour, wood flour, starch, rice bran, wheat bran, and soybean flour.

Examples of synthetic carriers include wet process silicas, dry process silicas, calcined products of wet process silicas, surface-modified silicas, and modified starch (Pineflow, available from Matsutani Chemical industry Co., Ltd.).

Examples of water-soluble carriers include water-soluble polymers, such as methyl cellulose, hydroxypropyl cellulose, hydroxypropyl methylcellulose, sodium carboxymethyl cellulose, propylene glycol alginate, polyvinylpyrrolidone, carboxyvinyl polymer, and casein sodium; urea, ammonium sulfate, sucrose, sodium chloride, salt cake, sodium carbonate, potassium carbonate, potassium pyrophosphate, sodium tripolyphosphate, maleic acid, fumaric acid, and malic acid.

When the water dispersible granules of the present invention comprise a carrier, the content of the carrier is usually from 1 to 30 wt %, preferably from 1 to 20 wt % with respect to the water dispersible granules of the present invention.

Examples of binders include dextrin, polyvinyl alcohol, gum arabic, sodium alginate, glucose, sucrose, and bentonite.

When the water dispersible granules of the present invention comprise a binder, the content of the binder is usually from 0.1 to 5 wt % with respect to the water dispersible granules of the present invention.

Examples of pH adjusters include citric acid and magnesium carbonate.

When the water dispersible granules of the present invention comprise a pH adjuster, the content of the pH adjuster is usually from 0.1 to 5 wt % with respect to the water dispersible granules of the present invention.

Examples of defoamers include silicone-based or fatty acid-based compounds.

When the water dispersible granules of the present invention comprise a defoamer, the content of the defoamer is usually from 0.01 to 5 wt % with respect to the water dispersible granules of the present invention.

Examples of nonionic surfactants may include sugar ester, fatty acid ester, polyoxyethylene alkyl ether, polyoxyethylene alkyl phenol, polyoxyethylene-polyoxypropylene block copolymer, polyoxyethylene alkylamine, polyoxyethylene bisphenol, polycyclic aromatics of polyoxyalkylene, silicon-based polyoxyethylene ether, silicon-based polyoxyethylene ester, fluorine-based polyoxyethylene ether, and fluorine-based polyoxyethylene ester. Specific examples include sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene castor oil, polyoxyethylene hydrogenated castor oil, polyoxyethylene alkyl phenyl ether, polyoxyethylene dialkyl phenyl ether, polyoxyethylene alkyl phenyl ether-formalin condensate, alkyl polyoxyethylene polyoxypropylene ether, polyoxyethylene polyoxypropylene alkyl aryl ether, polyoxyethylene polyoxypropylene tristyrylphenyl ether, polyoxyethylene styrylphenyl ether, polyoxyethylene tristyrylphenyl ether, polyalcohol fatty acid ester, polyoxyethylene polyhydric alcohol fatty acid ester, alkylphenyl polyoxyethylene polyoxypropylene ether, polyoxyethylene fatty acid amide, polyoxyalkylene benzylated phenyl, and polyoxyalkylene styrylated phenyl ether.

When the water dispersible granules of the present invention comprise a nonionic surfactant, the content of the nonionic surfactant is usually from 0.1 to 5 wt % with respect to the water dispersible granules of the present invention.

Examples of cationic surfactants may include alkylamine hydrochlorides, such as dodecylamine hydrochloride, alkyl quaternary ammonium salts, such as dodecyl trimethylammonium salt, alkyldimethyl benzylammonium salts, alkyl pyridinium salts, alkyl isoquinolinium salts, and dialkyl morpholinium salts; benzethonium chloride, and polyalkylvinylpyridinium salts. Examples of salts include chlorides, bromides, methylsulfates, and ethylsulfates.

When the water dispersible granules comprise a cationic surfactant, the content of the cationic surfactant is usually from 0.1 to 5 wt % with respect to the water dispersible granules of the present invention.

Examples of amphoteric surfactants may include N-lauryl alanine, N,N,N-trimethylaminopropionic acid, N,N,N-trihydroxyethylaminopropionic acid, N-hexyl-N,N-dimethylaminoacetic acid, 1-(2-carboxyethyl)pyridinium betaine, and lecithin.

When the water dispersible granules of the present invention comprise an amphoteric surfactant, the content of the amphoteric surfactant is usually from 0.1 to 5 wt % with respect to the water dispersible granules of the present invention.

The water dispersible granules of the present invention can be usually produced by the following procedure: mixing an agrochemical active ingredient that is solid at 25° C., a polyoxyalkylene alkyl ether phosphate or its salt, at least one anionic surfactant selected from the group consisting of arylsulfonates or their formaldehyde condensates, ligninsulfonates, and polycarboxylates, lactose, and optionally a formulation adjuvant; wet-kneading the mixture; and granulating the resulting kneaded material using an extrusion granulator, followed by sizing, drying, and sifting.

The water dispersible granules of the present invention are used in an ordinary manner, i.e., in the form of an aqueous dispersion in which the water dispersible granules are disintegrated and dispersed in water.

Since the water dispersible granules of the present invention can be disintegrated and dispersed in a smaller amount of water than typical, a concentrated aqueous dispersion of the water dispersible granules of the present invention in a very small amount of water can be also mixed into a paste fertilizer.

An agrochemical-containing paste fertilizer of the present invention can be produced using the water dispersible granules of the present invention and a paste fertilizer. That is, the agrochemical-containing paste fertilizer of the present invention comprises (a) an agrochemical active ingredient that is solid at 25° C.; (b) a polyoxyalkylene alkyl ether phosphate or its salt; (c) at least one anionic surfactant selected from the group consisting of arylsulfonates or their formaldehyde condensates, ligninsulfonates, and polycarboxylates; (d) lactose; and (e) a fertilizer ingredient.

The paste fertilizer may be a commercially available product. Examples of commercially available products include Neo Paste No. 1 (available from Katakura Chikkarin Co., Ltd.), New Flavor Paste (available from Katakura Chikkarin Co., Ltd.), Maroyaka Red No. 1 (available from Katakura Chikkarin Co., Ltd.), GU Power (available from Co-op Chemical Co., Ltd.), Eco Paste 220 (available from Co-op Chemical Co., Ltd.), Co-op Paste 222P (available from Co-op Chemical Co., Ltd.), and Taki Paste No. (available from Taki Chemical Co., Ltd.).

The agrochemical-containing paste fertilizer of the present invention can be usually produced by directly mixing the water dispersible granules of the present invention into the paste fertilizer, or by mixing into the paste fertilizer a concentrated aqueous dispersion in which the water dispersible granules of the present invention have been disintegrated and dispersed in a very small amount of water.

The weight ratio of the water dispersible granules of the present invention to water in the concentrated aqueous dispersion is usually from 1:0.5 to 1:2 (the water dispersible granules of the present invention:water), preferably from 1:0.8 to 1:1.2.

The content of the water dispersible granules of the present invention in the agrochemical active ingredient-containing paste fertilizer of the present invention is usually, but not necessarily, from 100 to 500 g for the amount of the paste fertilizer to be applied to 10 ares of paddy field, depending on the target crop, the soil conditions, and the type of paste fertilizer. It is noted that the paste fertilizer is usually applied in an amount of from 20 to 60 kg per 10 ares of paddy field.

The water dispersible granules of the present invention may be also used in a mixture with a liquid fertilizer.

The agrochemical-containing liquid fertilizer of the present invention can be produced using the water dispersible granules of the present invention and a liquid fertilizer. That is, the agrochemical-containing liquid fertilizer of the present invention comprises (a) an agrochemical active ingredient that is solid at 25° C.; (b) a polyoxyalkylene alkyl ether phosphate or its salt; (c) at least one anionic surfactant selected from the group consisting of arylsulfonates or their formaldehyde condensates, ligninsulfonates, and polycarboxylates; (d) lactose; and (e) a fertilizer ingredient.

EXAMPLES

The present invention is further described below by way of Production Examples and Test Examples.

First, Production Examples are described.

Production Example 1

Mixed were 20 parts by weight of isotianil, 15 parts by weight of clothianidin, 10 parts by weight of SS #80 (calcium carbonate, available from Nitto Funka Kogyo K.K.), 2 parts by weight of Newkalgen WG-2 (formaldehyde condensate of naphthalenesulfonate, available from TAKEMOTO OIL & FAT Co., Ltd.), and 52 parts by weight of Pharmatose 200M (lactose, available from DMV). The resulting mixture was subjected to dry grinding using a ZM-1 centrifugal mill (available from Retsch). To the resulting ground material were added 1 part by weight of Phosphanol RD-720 (containing about 55 wt % of sodium polyoxyethylene alkyl ether phosphate, available from TOHO Chemical Industry Co., Ltd.) and 10 parts by weight of water, followed by kneading with a mortar. The resulting kneaded material was extruded into granules using Dome-Gran DG-L1 (available from Fuji Paudal Co., Ltd.) equipped with a 0.8 mm φ screen, followed by drying and sifting to give water dispersible granules (hereinafter referred to as water dispersible granules 1).

Production Example 2

Water dispersible granules (hereinafter referred to as water dispersible granules 2) were obtained in the same manner as in Production Example 1 except that the amount of Pharmatose 200M was 51 parts by weight and the amount of Phosphanol RD-720 was 2 parts by weight.

Production Example 3

Water dispersible granules (hereinafter referred to as water dispersible granules 3) were obtained in the same manner as in Production Example 1 except that the amount of Pharmatose 200M was 52.5 parts by weight and the amount of Phosphanol RD-720 was 0.5 parts by weight.

Production Example 4

Water dispersible granules (hereinafter referred to as water dispersible granules 4) were obtained in the same manner as in Production Example 1 except that the amount of Pharmatose 200M was 45.7 parts by weight, the amount of Phosphanol RD-720 was 7.3 parts by weight, and the amount of water was 12 parts by weight.

Production Example 5

Water dispersible granules (hereinafter referred to as water dispersible granules 5) were obtained in the same manner as in Production Example 1 except that the amount of Newkalgen WG-2 was 1 part by weight, the amount of Pharmatose 200M was 51 parts by weight, the amount of Phosphanol RD-720 was 3 parts by weight, and the amount of water was 12 parts by weight.

Production Example 6

Water dispersible granules (hereinafter referred to as water dispersible granules 6) were obtained in the same manner as in Production Example 1 except that the amount of Pharmatose 200M was 49.3 parts by weight, the amount of Phosphanol RD-720 was 3.7 parts by weight, and the amount of water was 12 parts by weight.

Production Example 7

Water dispersible granules (hereinafter referred to as water dispersible granules 7) were obtained in the same manner as in Production Example 1 except that the amount of Newkalgen WG-2 was 1.5 parts by weight, the amount of Pharmatose 200M was 51.7 parts by weight, the amount of Phosphanol RD-720 was 1.8 parts by weight (containing about 55 wt % of sodium polyoxyethylene alkyl ether phosphate, available from TOHO Chemical Industry Co., Ltd.), and the amount of water was 12 parts by weight.

Production Example 8

Water dispersible granules (hereinafter referred as water dispersible granules 8) were obtained in the same manner as in Production Example 1 except that the amount of Newkalgen WG-2 was 5.5 parts by weight, the amount of Pharmatose 200M was 48.5 parts by weight, and the amount of water was 12 parts by weight.

Production Example 9

Water dispersible granules (hereinafter referred as water dispersible granules 9) were obtained in the same manner as in Production Example 1 except that no SS #80 was used, the amount of Pharmatose 200M was 62 parts by weight, and the amount of water was 14 parts by weight.

Production Example 10

Water dispersible granules (hereinafter referred as water dispersible granules 10) were obtained in the same manner as in Production Example 1 except that no SS #80 was used, 52 parts by weight of Pharmatose 200M were replaced with 62 parts by weight of Pharmatose 80M (lactose, available from DMV), and the amount of water was 14 parts by weight.

Production Example 11

Mixed were 60 parts by weight of isotianil, 4 parts by weight of Newkalgen WG-2 (formaldehyde condensate of naphthalenesulfonate, available from TAKEMOTO OIL & FAT Co., Ltd.), and 35 parts by weight of Pharmatose 200M (lactose, available from DMV). The resulting mixture was subjected to dry grinding using a ZM-1 centrifugal mill (available from Retsch). To the resulting ground material were added 1 part by weight of Phosphanol RD-720 (containing about 55 wt % of sodium polyoxyethylene alkyl ether phosphate, available from TOHO Chemical Industry Co., Ltd.) and 12 parts by weight of water, followed by kneading with a mortar. The resulting kneaded material was extruded into granules using DomeGran DG-L1 (available from Fuji Paudal Co., Ltd.) equipped with a 0.8 mm φ screen, followed by drying and sifting to give water dispersible granules (hereinafter referred to as water dispersible granules 11).

Production Example 12

Mixed were 35 parts by weight of furametpyr, 2 parts by weight of Newkalgen WG-2 (formaldehyde condensate of naphthalenesulfonate, available from TAKEMOTO OIL & FAT Co., Ltd.), and 62 parts by weight of Pharmatose 200M (lactose, available from DMV). The resulting mixture was subjected to dry grinding using a ZM-1 centrifugal mill (available from Retsch). To the resulting ground material were added 1 part by weight of Phosphanol RD-720 (containing about 55 wt % of sodium polyoxyethylene alkyl ether phosphate, available from TOHO Chemical Industry Co., Ltd.) and 12 parts by weight of water, followed by kneading with a mortar. The resulting kneaded material was extruded into granules using DomeGran DG-L1 (available from Fuji Paudal Co., Ltd.) equipped with a 0.8 mm φ screen, followed by drying and sifting to give water dispersible granules (hereinafter referred to as water dispersible granules 12).

Production Example 13

Water dispersible granules (hereinafter referred as water dispersible granules 13) were obtained in the same manner as in Production Example 12 except that 35 parts by weight of furametpyr were replaced with 35 parts by weight of cartap.

Production Example 14

Water dispersible granules (hereinafter referred as water dispersible granules 14) were obtained in the same manner as in Production Example 12 except that 35 parts by weight of furametpyr were replaced with 35 parts by weight of cartap and 1 part by weight of Phosphanol RD-720 was replaced with 1 part by weight of Phosphanol RS-710 (containing about 90 wt % of polyoxyethylene alkyl ether phosphate, available from TOHO Chemical Industry Co., Ltd.).

Production Example 15

Water dispersible granules (hereinafter referred as water dispersible granules 15) were obtained in the same manner as in Production Example 1 except that no SS #80 was used and 2 parts by weight of Newkalgen WG-2 were replaced with 2 parts by weight of Newkalgen BX-C (alkylnaphthalenesulfonate, available from TAKEMOTO OIL & FAT Co., Ltd.), the amount of Pharmatose 200M was 62 parts by weight, and the amount of water was 12 parts by weight.

Production Example 16

Water dispersible granules (hereinafter referred as water dispersible granules 16) were obtained in the same manner as in Production Example 1 except that no SS #80 was used and 2 parts by weight of Newkalgen WG-2 were replaced with 2 parts by weight of DEMOL SN-B (formaldehyde condensate of alkylnaphthalenesulfonate, available from Kao Corporation), the amount of Pharmatose 200M was 62 parts by weight, and the amount of water was 12 parts by weight.

Production Example 17

Water dispersible granules (hereinafter referred as water dispersible granules 17) were obtained in the same manner as in Production Example 1 except that no SS #80 was used and 2 parts by weight of Newkalgen WG-2 were replaced with 2 parts by weight of Newkalgen WG-4 (sodium ligninsulfonate, available from TAKEMOTO OIL & FAT Co., Ltd.), the amount of Pharmatose 200M was 62 parts by weight, and the amount of water was 11 parts by weight.

Production Example 18

Water dispersible granules (hereinafter referred as water dispersible granules 18) were obtained in the same manner as in Production Example 1 except that no SS #80 was used and 2 parts by weight of Newkalgen WG-2 were replaced with 2 parts by weight of Newkalgen WG-5 (polycarboxylate, available from TAKEMOTO OIL & FAT Co., Ltd.), the amount of Pharmatose 200M was 62 parts by weight, and the amount of water was 12 parts by weight.

Test Example 1

The water dispersible granules 1 to 18 (0.5 g for each) were placed in a 100 mL graduated cylinder with a stopper containing 100 mL of hard water (20° C.) having a hardness of 3 degrees. The graduated cylinder was immediately inverted once every two seconds, and the number of inversions required for complete disintegration of the water dispersible granules was measured.

The results are shown in Table 1. The water dispersible granules 1 to 18 all exhibited good underwater disintegrability.

Test Example 2

The water dispersible granules 1 to 18 were stored at 54° C. for two weeks, and the underwater disintegrability test was carried out in the same manner as in Test Example 1.

The results are shown in Table 1. The water dispersible granules 1 to 18 all exhibited little degradation in underwater disintegrability.

Test Example 3

The water dispersible granules 1 to 18 (5 g for each) were precisely weighed (A g), and placed in a stainless steel cylindrical ball mill pot (diameter 90 mm, height 90 mm) containing ten stainless steel balls (weight 16.64 g/ball, diameter 15.9 mm). The ball mill pot was closed with a lid, placed on a roller, and rotated at a speed of 23 to 24 rev/min for 3 minutes. The water dispersible granules were then taken out of the ball mill pot, and sifted through a sieve with a mesh size of 300 μm. Residual water dispersible granules on the sieve with a mesh size of 300 μm were weighed (B g), and the disintegration rate was determined according to the following equation.

Disintegration Rate [%]=(A−B)/A×100

The results are shown in Table 1. The water dispersible granules 1 to 18 all had low disintegration rate, and had good granule hardness.

Test Example 4

The water dispersible granules 1 to 18 were stored at 54° C. for two weeks, and the disintegration rate was measured in the same manner as in Test Example 3.

The results are shown in Table 1. The water dispersible granules 1 to 18 all exhibited little change in disintegration rate, and had no significant degradation in granule hardness.

the water dispersible granules 1 were readily disintegrated and dispersed. The resulting dispersion (1.0 g) was added to 100 g of a commercially available paste fertilizer, Neo Paste No. 1 (available from Katakura Chikkarin Co., Ltd.), New Flavor Paste (available from Katakura Chikkarin Co., Ltd.), Maroyaka Red No. 1 (available from Katakura Chikkarin Co., Ltd.), GU Power (available from Co-op Chemical Co., Ltd.), Eco Paste 220 (available from Co-op Chemical Co., Ltd.), Co-op Paste 222P (available from Co-op Chemical Co., Ltd.), or Taki Paste No. 12 (available from Taki Chemical Co., Ltd.), and mixed for 1 minute, followed by sifting through a sieve with a mesh size of 250 μm. No solid material or paste residue remained on the sieve, which indicated good dispersibility and miscibility of 1:1 aqueous dilutions of the water dispersible granules in the paste fertilizers.

The water dispersible granules of the present invention are useful formulations that have good disintegrability and dispersibility as well as good storage stability and that can be also used for producing agrochemical-containing paste fertilizers and agrochemical-containing liquid fertilizers.

The invention claimed is:

1. Water dispersible granules, comprising:
   (a) an agrochemical active ingredient that is solid at 25° C.;
   (b) a polyoxyalkylene alkyl ether phosphate or its salt;
   (c) at least one anionic surfactant selected from the group consisting of arylsulfonates or their formaldehyde condensates, ligninsulfonates, and polycarboxylates; and
   (d) lactose.

2. The water dispersible granules according to claim 1, comprising:
   1 to 80 wt % of (a) the agrochemical active ingredient that is solid at 25° C.;
   0.1 to 10 wt % of (b) the polyoxyalkylene alkyl ether phosphate or its salt;
   0.1 to 20 wt % of the total of (c) the at least one anionic surfactant selected from the group consisting of arylsulfonates or their formaldehyde condensates, ligninsulfonates, and polycarboxylates; and
   10 to 98.8 wt % of (d) lactose.

3. The water dispersible granules according to claim 2, comprising:

TABLE 1

|  |  | water dispersible granules | | | | | | | | |
|---|---|---|---|---|---|---|---|---|---|---|
|  |  | 1 | 2 | 3 | 4 | 5 | 6 | 7 | 8 | 9 |
| underwater disintegrability [times] | initial | 4 | 9 | 3 | 15 | 9 | 9 | 5 | 6 | 4 |
|  | 54° C. 2 W | 5 | 9 | 3 | 15 | 10 | 10 | 5 | 8 | 4 |
| disintegration rate [%] | initial | 4.6 | 2.0 | 4.8 | 1.0 | 6.8 | 1.6 | 5.6 | 1.8 | 1.6 |
|  | 54° C. 2 W | 4.0 | 3.0 | 6.2 | 1.7 | 11.0 | 2.2 | 6.8 | 2.6 | 1.4 |

|  |  | water dispersible granules | | | | | | | | |
|---|---|---|---|---|---|---|---|---|---|---|
|  |  | 10 | 11 | 12 | 13 | 14 | 15 | 16 | 17 | 18 |
| underwater disintegrability [times] | initial | 4 | 6 | 6 | 3 | 3 | 5 | 3 | 5 | 7 |
|  | 54° C. 2 W | 7 | 7 | 11 | 5 | 4 | 3 | 4 | 3 | 8 |
| disintegration rate [%] | initial | 1.6 | 4.8 | 7.8 | 5.4 | 4.2 | 5.2 | 1.8 | 5.2 | 0.6 |
|  | 54° C. 2 W | 3.0 | 3.8 | 4.2 | 3.0 | 5.0 | 2.8 | 3.4 | 6.8 | 0.2 |

Test Example 5

To 2.5 g of the water dispersible granules 1, 2.5 g of water was added and mixed with a spatula for 1 minute. As a result, 0.1 to 10 wt % of the total of (c) the at least one anionic surfactant selected from the group consisting of arylsulfonates or their formaldehyde condensates, ligninsulfonates, and polycarboxylates.

4. The water dispersible granules according to claim 1, wherein the weight ratio of (b) the polyoxyalkylene alkyl ether phosphate or its salt to the total of (c) the at least one anionic surfactant selected from the group consisting of arylsulfonates or their formaldehyde condensates, ligninsulfonates, and polycarboxylates is from 1:0.5 to 1:15.

5. The water dispersible granules according to claim 1, wherein the weight ratio of (b) the polyoxyalkylene alkyl ether phosphate or its salt to the total of (c) the at least one anionic surfactant selected from the group consisting of arylsulfonates or their formaldehyde condensates, ligninsulfonates, and polycarboxylates is from 1:0.5 to 1:10.

6. The water dispersible granules according to claim 1, wherein the weight ratio of (b) the polyoxyalkylene alkyl ether phosphate or its salt to the total of (c) the at least one anionic surfactant selected from the group consisting of arylsulfonates or their formaldehyde condensates, ligninsulfonates, and polycarboxylates is from 1:1.5 to 1:7.5.

7. The water dispersible granules according to claim 1, wherein (b) the polyoxyalkylene alkyl ether phosphate or its salt is a sodium salt of polyoxyalkylene alkyl ether phosphate.

8. The water dispersible granules according to claim 1, wherein (c) the at least one anionic surfactant selected from the group consisting of arylsulfonates or their formaldehyde condensates, ligninsulfonates, and polycarboxylates is an arylsulfonate or its formaldehyde condensate.

9. The water dispersible granules according to claim 8, wherein the arylsulfonate or its formaldehyde condensate is a formaldehyde condensate of sodium naphthalenesulfonate.

10. The water dispersible granules according to claim 9, wherein the formaldehyde condensate of naphthalenesulfonate is a formaldehyde condensate of sodium naphthalenesulfonate.

11. The water dispersible granules according to claim 1, wherein (a) the agrochemical active ingredient that is solid at 25° C. is an insecticidal ingredient and/or fungicidal ingredient.

12. The water dispersible granules according to claim 11, wherein (a) the agrochemical active ingredient that is solid at 25° C. is at least one selected from the group consisting of neonicotinoid insecticides, nereistoxin insecticides, fungicides having an activity against *Magnaporthe grisea*, and fungicides having an activity against *Rhizoctonia solani*.

13. The water dispersible granules according to claim 11, wherein (a) the agrochemical active ingredient that is solid at 25° C. is at least one selected from the group consisting of neonicotinoid insecticides and fungicides having an activity against *Magnaporthe grisea*.

14. The water dispersible granules according to claim 12, wherein (a) the agrochemical active ingredient that is solid at 25° C. is at least one selected from the group consisting of clothianidin, cartap, isotianil, and furametpyr.

15. The water dispersible granules according to claim 13, wherein (a) the agrochemical active ingredient that is solid at 25° C. is at least one selected from the group consisting of clothianidin and isotianil.

16. A method for producing water dispersible granules, comprising:
adding water to a mixture containing:
(a) an agrochemical active ingredient that is solid at 25° C.;
(b) a polyoxyalkylene alkyl ether phosphate or its salt;
(c) at least one anionic surfactant selected from the group consisting of arylsulfonates or their formaldehyde condensates, ligninsulfonates, and polycarboxylates; and
(d) lactose;
kneading the mixture; and
granulating the kneaded mixture by a wet extrusion granulation method.

17. A method for producing an agrochemical-containing paste fertilizer or agrochemical-containing liquid fertilizer, comprising a step of:
mixing the water dispersible granules according to claim 1 with a paste fertilizer or liquid fertilizer.

18. An agrochemical-containing paste fertilizer, comprising:
(a) an agrochemical active ingredient that is solid at 25° C.;
(b) a polyoxyalkylene alkyl ether phosphate or its salt;
(c) at least one anionic surfactant selected the group consisting of arylsulfonates or their formaldehyde condensates, ligninsulfonates, and polycarboxylates;
(d) lactose; and
(e) a fertilizer ingredient.

19. An agrochemical-containing liquid fertilizer, comprising:
(a) an agrochemical active ingredient that is solid at 25° C.;
(b) a polyoxyalkylene alkyl ether phosphate or its salt;
(b) a polyoxyalkylene alkyl ether phosphate or its salt;
(c) at least one anionic surfactant selected the group consisting of arylsulfonates or their formaldehyde condensates, ligninsulfonates, and polycarboxylates;
(d) lactose; and
(e) a fertilizer ingredient.

20. A method for applying an agrochemical, comprising:
side-dressing the agrochemical-containing paste fertilizer according to claim 18.

21. A method for applying an agrochemical, comprising:
side-dressing the agrochemical-containing liquid fertilizer according to claim 19.

* * * * *